United States Patent [19]

Hunkeler et al.

[11] Patent Number: 5,021,411
[45] Date of Patent: * Jun. 4, 1991

[54] IMIDAZODIAZEPINE DERIVATIVES

[75] Inventors: Walter Hunkeler, Magden; Emilio Kyburz, Reinach, both of Switzerland; Marc Meier, Village-Neuf, France

[73] Assignee: Hoffmann-La Roche Inc., Nutley, N.J.

[*] Notice: The portion of the term of this patent subsequent to Sep. 5, 2006 has been disclaimed.

[21] Appl. No.: 396,884

[22] Filed: Aug. 22, 1989

[30] Foreign Application Priority Data

Aug. 31, 1988 [CH] Switzerland .................. 3237/88
Jun. 5, 1989 [CH] Switzerland .................. 2108/89

[51] Int. Cl.$^5$ ................ C07D 487/08; C07D 495/14; A61K 31/55
[52] U.S. Cl. ..................................... 514/220; 540/498
[58] Field of Search ...................... 540/498; 514/220

[56] References Cited

U.S. PATENT DOCUMENTS

| | | | |
|---|---|---|---|
| 4,316,839 | 2/1982 | Gerecke et al. | 540/498 |
| 4,346,030 | 8/1982 | Gerecke | 540/498 |
| 4,616,010 | 10/1986 | Hunkeler et al. | 540/498 |
| 4,775,671 | 10/1988 | Hunkeler et al. | 540/448 |
| 4,803,920 | 9/1989 | Hunkeler | 514/219 |

Primary Examiner—Robert Gerstl
Attorney, Agent, or Firm—George M. Gould; George W. Johnston; Alan P. Kass

[57] ABSTRACT

Imidazodiazepine derivatives of the formula

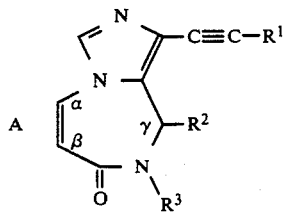

wherein A together with the two carbon atoms denoted by α and β represent one of the following groups

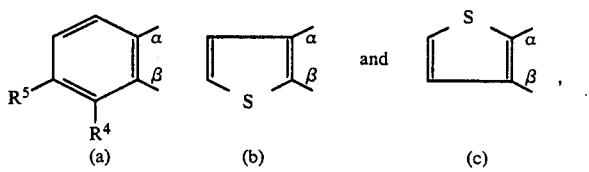

$R^1$ is a partially unsaturated lower hydrocarbon group which is optionally substituted with hydroxy, oxo, aryl or the group —OR, —SR or —OCOR or a lower alkyl group which is substituted with aryl or the group —OR', —SR' or —OCOR'. R and R' each represents aryl or a saturated or partially unsaturated $C_{1-18}$-hydrocarbon group which is optionally substituted with aryl or lower alkoxy, $R^2$ is hydrogen and $R^3$ is lower alkyl or $R^2$ and $R^3$ together represent dimethylene or trimethylene and $R^4$ and $R^5$ each is hydrogen, halogen, trifluoromethyl, cyano, nitro or lower alkyl, the group —OR' being different from lower alkoxy and the compounds of formula I having the (S)- or (R,S)-configuration with reference to the carbon atom denoted by γ when $R^2$ and $R^3$ together represent dimethylene or trimethylene, can be used in the control or prevention of convulsions, sleep disorders, or in the partial or complete selective antagonism of some or all activities which 1,4-benzodiazepines having tranquillizing activity or other substances exhibit via the central benzodiazepine receptors.

33 Claims, No Drawings

IMIDAZODIAZEPINE DERIVATIVES

SUMMARY OF THE INVENTION

The present invention is concerned with imidazodiazepine derivatives. In particular, it provides imidazodiazepine derivatives of the formula

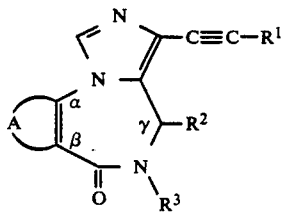
I wherein A together with the two carbon atoms denoted by α and β represents one of the following groups:

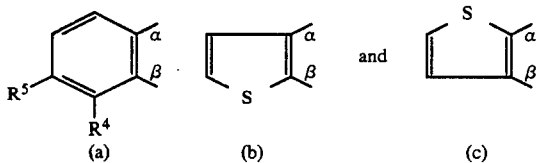

$R^1$ is a partially unsaturated lower hydrocarbon group which is optionally substituted with hydroxy, oxo, aryl or the group —OR, —SR or —OCOR, or $R^1$ is a lower alkyl group which is substituted with aryl or the group —OR', —SR' or —OCOR', R and R' each represents aryl or a saturated or partially unsaturated $C_{1-18}$-hydrocarbon group which is optionally substituted with aryl or lower alkoxy, $R^2$ is hydrogen, $R^3$ is lower alkyl or $R^2$ and $R^3$ together represent dimethylene or trimethylene, and $R^4$ and $R^5$ each represents hydrogen, halogen, trifluoromethyl, cyano, nitro or lower alkyl, the group —OR' being different from lower alkoxy and the compounds of formula I having the (S)- or (R,S)-configuration with reference to the carbon atom denoted by γ when $R^2$ and $R^3$ together represent dimethylene or trimethylene. These compounds are novel and are characterized by valuable pharmacodynamic properties.

Objects of the present invention are the compounds of formula I above per se and as therapeutically active substances, a process for their manufacture, medicaments containing a compound of formula I and a therapeutically inert carrier, the manufacture of such medicaments and the use of compounds of formula I in the control or prevention of illnesses (especially in the control or prevention of convulsions, anxiety states, stress conditions, excitation states and sleep disorders and/or in the partial or complete selective antagonism of some or all activities which 1.4-benzodiazepines having tranquillizing activity or other substances display via the central benzodiazepine receptors) and, respectively, the use of compounds of formula I for the manufacture of medicaments, especially of medicaments for use in the just-mentioned indications.

DETAILED DESCRIPTION OF THE INVENTION

The term "lower" is used to refer residues and compounds having from 1 to 7, preferably 1 to 4, carbon atoms. The term "alkyl" means straight-chain or branched saturated hydrocarbon residues such as methyl, ethyl, n-propyl, isopropyl, n-butyl, isobutyl, s-butyl, t-butyl and the like. The term "alkoxy" refers to alkyl residues in the sense of the previous definition of the term "alkyl" which are attached via an oxygen atom. The term "alkenyl" refers to straight-chain or branched hydrocarbon residues which contain at least one olefinic double bond such as cis- and trans-2-buten-2-yl and 1-buten-3-yl. The term "aryl" means monocyclic aromatic hydrocarbon residues which are preferably unsubstituted or substituted with lower alkyl, lower alkoxy and/or halogen. Unless indicated otherwise, the term "halogen" denotes the four halogens fluorine, chlorine, bromine and iodine.

The term "hydrocarbon group" denotes open-chain and cyclic groups and combinations thereof. The open-chain groups can be straight-chain or branched. Examples of saturated lower hydrocarbon groups are: methyl, ethyl, i-propyl, t-butyl, 3-pentyl, 1-nonyl, cyclopropyl, cyclopentyl, cyclohexyl, cyclopropylmethyl, cyclohexylmethyl and 1-cyclopropylethyl. Examples of unsaturated hydrocarbon groups are, for example, the above-mentioned alkenyl groups, especially lower alkenyl groups, or hydrocarbon residues which contain at least one acetylenic triple bond, i.e. alkynyl, especially lower alkynyl, e.g. 1-propyn-3-yl.

$R^1$ preferably is a lower alkenyl group which is optionally substituted with hydroxy, oxo, aryl or the group —OR, —SR or —OCOR, or a lower alkyl group which is substituted with aryl or the group —OR', —SR' or —OCOR', especially a lower alkenyl group which is substituted with hydroxy or the group —OR, —SR or —OCOR or a lower alkyl group which is substituted with the group —OR', —SR' or —OCOR'. Preferably R and R' each represents aryl, aryl-lower alkyl, lower alkoxy-lower alkyl, lower alkyl, $C_{3-7}$-cycloalkyl or $C_{3-7}$-cycloalkyl-lower alkyl.

When $R^2$ is hydrogen and $R^3$ s lower alkyl, then $R^3$ preferably stands for methyl. When $R^2$ and $R^3$ together represent dimethylene or trimethylene, then the carbon atom denoted by γ preferably has the (S)-configuration.

When A is a residue of formula (a). then preferably one of $R^4$ and $R^5$ is hydrogen and the other is hydrogen or halogen; thus, for example. $R^4$ and $R^5$ both represent hydrogen or $R^4$ is hydrogen and $R^5$ is fluorine, or $R^4$ is chlorine or bromine and $R^5$ is hydrogen.

Preferred compounds of formula I within the scope of the present invention are:

7-Chloro-3-[3-(cyclopropylmethoxy)-1-propynyl]-4,5-dihydro-5-methyl-6H-imidazo[1,5-a][1,4]benzodiazepin-6-one.

3-(7-chloro-5,6-dihydro-5-methyl-6-oxo-4H-imidazo-[1.5-a][1.4]benzodiazepin-3-yl)-2-propynyl acetate.

7-chloro-3-[3-(cyclopropylmethoxy)-3-methyl-1-butynyl]-5-methyl-6H-imidazo[1,5-a][1,4]benzodiazepin-6-one.

7-chloro-4,5-dihydro-3-[(Z)-5-hydroxy-3-methyl-3-penten-1-ynyl]-5-methyl-6H-imidazo[1,5-a][1,4]benzo-diazepin-6-one.

7-chloro-4,5-dihydro-3-(3-hydroxy-3-methyl-4-penten-1-ynyl)-5-methyl-6H-imidazo[1,5-a][1,4]benzodiazepin-6-one and 7-chloro-3-[(E)-5-hydroxy-3-methyl-3-penten-1-ynyl]-5-methyl-6H-imidazo[1,5-a][1,4]benzodiazepin-6-one.

The compounds of formula I can be prepared as follows:

(a) reacting compound of the formula

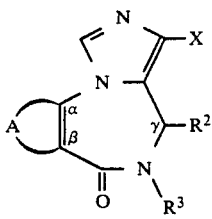

wherein A, $R^2$ and $R^3$ have the above meanings and X is bromine or iodine, with the proviso that where A is a residue of formula (a) and $R^4$ and/or $R^5$ is halogen, this halogen is fluorine or chlorine when X is bromine or is fluorine, chlorine or bromine when X is iodine, with a compound of the formula

HC≡C—$R^1$ wherein $R^1$ has the above meaning;
or (b) etherifying or acylating a compound of formula I in which $R^1$ is a partially unsaturated lower hydrocarbon group which is substituted with hydroxy or a compound of the formula

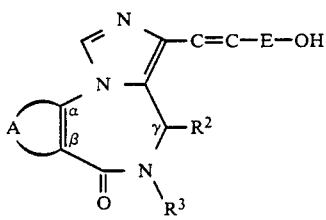

wherein E is lower alkylene and $R^2$, $R^3$ and A have the above meanings,
with an agent yielding the group —OR or —OCOR or the group —OR' or —OCOR'.

The reaction of compounds of formulae II and III in accordance with process aspect (a) is effected in the presence of a palladium(II) salt such as palladium chloride or palladium acetate, of an organophosphine such as triphenylphosphine, of copper(I) iodide and of a secondary or tertiary amine such as diethylamine or triethylamine. In place of a palladium(II) salt and an organophosphine there can also be used a suitable corresponding complex such as bis(triphenylphosphine) palladium(II) dichloride. As the solvent there can be used the aforementioned secondary or tertiary amine itself, a halogenated hydrocarbon such as methylene chloride, N,N-dimethylformamide or a mixture thereof. The reaction is effected at temperatures in a range between about room temperature and about 120° C., with the reflux temperature being preferred. Depending on the remaining reaction parameters, the reaction time can be from about 1 to about 70 hours. The starting materials of formula II are known or can be prepared readily according to methods which are known to those skilled in the art.

In accordance with process aspect (b) a hydroxy group is etherified or acylated. This is thus an etherification or acylation of a hydroxy group, and methods for carrying out such an etherification are known to those skilled in the art. A corresponding halide especially a chloride or bromide, is conveniently used as the etherifying or acylating agent. In the case of the etherification, this is conveniently carried out in the presence of a base, for example, an alkali metal hydroxide such as potassium hydroxide, and in the presence of an organic solvent which is inert under the reaction conditions, for example, N,N-dimethylformamide, dimethyl sulphoxide, toluene or the like. In the case of the acylation, this is conveniently carried out in the presence of an acid-binding agent, for example, a tertiary amine such as pyridine, which can simultaneously serve as the solvent. The reaction temperature is in a range from about −10° C. to about 50° C.

The compounds of formula IV which are used as starting materials can be prepared by analogy to process variant (a) from compounds of formula II and compounds of the formula HC≡C—E—OH in which E has the above significance.

As mentioned previously, the compounds of formula I are novel. They possess valuable pharmacodynamic properties and have only a low toxicity. They are characterized by a pronounced affinity to the central benzodiazepine receptors and possess either pronounced anxiolytic, anticonvulsant, muscle relaxant and sedative-hypnotic properties and/or they partially or completely selectively antagonize some or all activities which 1,4-benzodiazepines having tranquillizing activity or other substances exhibit via the central benzodiazepine receptors.

The affinity of compounds of formula I to the central benzodiazepine receptors has been determined according to the method described in Life Science 20, 2101–2110 (1977) and Science 198, 849–851 (1977). According to this method, the inhibition of the binding of tritiated diazepam at the specific benzodiazepine receptors in the cerebral cortex by the respective test substances is ascertained. The $IC_{50}$ ("50% inhibiting concentration") is that concentration of the respective test substance which brings about a 50 percent inhibition of the specific binding of the tritiated diazepam at the specific benzodiazepine receptors in the cerebral cortex.

The results obtained with representative compounds of formula I are reported in the following Table.

| Compound | Affinity to benzodiazepine receptors IC 50, nmol/l |
| --- | --- |
| A | 1.4 |
| B | 2.6 |
| C | 5.0 |
| D | 1.4 |
| E | 3.7 |
| F | 2.2 |

A = 7-Chloro-3-[3-(cyclopropylmethoxy)-1-propynyl]-4,5-dihydro-5-methyl-6H-imidazo[1,5-a][1,4]benzodiazepin-6-one
B = 3-(7-Chloro-5,6-dihydro-5-methyl-6-oxo-4H-imidazo-[1,5-a][1,4]benzodiazepin-3-yl)-2-propynyl acetate
C = 7-Chloro-3-[3-(cyclopropylmethoxy)-3-methyl-1-butynyl]-4,5-dihydro-5-methyl-6H-imidazo[1,5-a][1,4]benzodiazepin-6-one
D = 7-Chloro-4,5-dihydro-3-[(Z)-5-hydroxy-3-methyl-3-penten-1-ynyl]-5-methyl-6H-imidazo[1,5-a][1,4]benzodiazepine-6-one
E = 7-Chloro-4,5-dihydro-3-(3-hydroxy-3-methyl-4-penten-1-ynyl)-5-methyl-6H-imidazo[1,5-a][1,4]benzodiazepin-6-one
F = 7-Chloro-4,5-dihydro-3-[(E)-5-hydroxy-3-methyl-3-penten-1-ynyl]-5-methyl-6H-imidazo[1,5-a][1,4]benzodiazepin-6-one.

The compounds of formula I can be used in the form of pharmaceutical preparations which are another aspect of the invention. The pharmaceutical preparations can be administered orally. e.g., in the form of tablets, coated tablets, dragees, hard and soft gelatine capsules, solutions, emulsions or suspensions. The administration can, however, also be carried out rectally, e.g., in the form of suppositories, or parenterally, e.g., in the form of injection solutions.

For the preparation of pharmaceutical preparations the compounds of formula I can be processed with pharmaceutically inert, inorganic or organic carriers. Lactose, maize starch or derivatives thereof, talc, stearic acid or its salts and the like can be used, for example, as carriers for tablets, coated tablets, dragees and hard gelatine capsules. Suitable carriers for soft gelatine capsules are, for example, vegetable oils, waxes, fats, semisolid and liquid polyols and the like. Depending on the nature of the active substance no carriers are, however, generally required in the case of soft gelatine capsules. Suitable carriers for solutions and syrups are, for example, water, polyols, saccharose, invert sugar, glucose and the like. Suitable carriers for injection solutions are, for example, water, alcohols, polyols, glycerol, vegetable oils and the like. Suitable carriers for suppositories are, for example, natural or hardened oils, waxes, fats, semi-liquid or liquid polyols and the like.

The pharmaceutical preparations can also contain preserving agents, solubilizing agents, stabilizing agents, wetting agents, emulsifying agents, sweetening agents, coloring agents, flavoring agents, salts for varying the osmotic pressure, buffers, coating agents or antioxidants. They can also contain still other therapeutically useful substances.

As mentioned previously, the compounds of formula I can be used in accordance with the invention in the control or prevention of illnesses, especially in the control of convulsions and anxiety states and/or in the partial or complete antagonism of some or all activities which 1,4-benzodiazepines having tranquillizing activity or other substances display via the central benzodiazepine receptors. The dosage can vary within wide limits and will, of course, be adjusted to the individual requirements in each particular case. In general, in the case of oral administration a daily dosage of about 0.1 mg to 100 mg should be sufficient. The following Examples are intended to illustrate the present invention in more detail, but are not intended to limit its extent in any manner. All temperatures are given in degrees Celsius.

EXAMPLE 1

(a) 5.20 g (14 mmol) of 7-chloro-4,5-dihydro-3-iodo-5-methyl-6H-imidazo[1,5-a][1,4]benzodiazepin-6-one were heated to boiling under reflux for 4 hours with 1.04 g (18.5 mmol) of propargyl alcohol, 70 mg of bis-(triphenyl -phosphine)-palladium(II) dichloride and 10 mg of copper(I) iodide in 35 ml of diethylamine. The reaction mixture was evaporated and the residue was suspended in methylene chloride. The suspension was suction filtered and the suction filter cake was washed with ethyl acetate. After two successive recrystallizations from ethanol and, respectively, N,N-dimethylformamide there was obtained 7-chloro-4,5-dihydro-3-(3-hydroxy-1-propynyl)-5-methyl-6H -imidazo[1,5-a][1,4]benzodiazepin-6-one of melting point 250-252°.

(b) 4.5 g (15 mmol) of 7-chloro-4,5-dihydro-3-(3-hydroxy -1-propynyl)-5-methyl-6H-imidazo[1,5-a][1,4]benzodiazepin -6-one were suspended in 30 ml of pyridine and treated dropwise at 0 to 5° C. within 15 minutes with 4.1 ml (20 mmol) of capryl chloride. The cooling bath was removed and the mixture was left to stir at room temperature for 1.5 hours. The reaction mixture was then poured into 300 ml of water and acidified to pH 1 with 30 ml of concentrated hydrochloric acid. The mixture was extracted three times with methylene chloride, the combined organic extracts were dried over magnesium sulphate and evaporated. By chromatography of the residue on silica gel while eluting with ethyl acetate/methylene chloride (1/3) and crystallization from methylene chloride, petroleum ether and hexane, there was obtained 1.55 g (22%) of 3-(7-chloro-5,6-dihydro-5-methyl-6-oxo-4H-imidazo[1,5-a][1,4]benzodiazepin-3-yl)-2-propynyl decanoate of melting point 70-72°.

In an analogous manner, from 7-chloro-4,5-dihydro-3-(3-hydroxy-1-propynyl)-5-methyl-6H-imidazo[1,5-a][1,4]-benzodiazepin-6-one (c) with pivaloyl chloride there was prepared 3-(7-chloro-5,6-dihydro-5-methyl-6-oxo-4H-imidazo[1,5-a][1,4]-benzodiazepin-3-yl)-2-propynyl pivalate of melting point 143-145° (from ethyl acetate);

(d) with acetyl chloride there was prepared 3-(7-chloro-5,6-dihydro-5-methyl-6-oxo-4H-imidazo[1,5-a][1,4]benzodiazepin-3-yl)-2-propynyl acetate of melting point 194-195° (from methylene chloride and ethyl acetate);

(e) with cyclohexanecarbonyl chloride there was prepared 3-(7-chloro-5,6-dihydro-5-methyl-6-oxo-4H-imidazo[1,5-a][1,4]benzodiazepin-3-yl)-2-propynyl cyclohexanecarboxylate of melting point 143-144° (from ethyl acetate and hexane);

(f) with benzoyl chloride there was prepared 3-(7-chloro -5,6-dihydro-5-methyl-6-oxo-4H-imidazo[1,5-a][1,4]benzodiazepin-3-yl)-2-propynyl benzoate of melting point 152-154° (from ethyl acetate);

(g) with cyclopropanecarbonyl chloride there was prepared 3-(7-chloro-5,6-dihydro-5-methyl-6-oxo-4H-imidazo[1,5-a][1,4]benzodiazepin-3-yl)-2-propynyl cyclopropanecarboxylate of melting point 120-121° (from ethyl acetate).

EXAMPLE 2

(a) 3.34 g (59 mmol) of freshly powdered potassium hydroxide were suspended in 25 ml of N,N-dimethylformamide and treated with 4.0 g (13.2 mmol) of 7-chloro-4,5-dihydro-3-(3-hydroxy-1-propynyl)-5-methyl-6H-imidazo[1,5-a][1,4]benzodiazepin-6-one. After stirring at room temperature for 5 minutes the mixture was cooled to 2°, whereupon 4.95 g (31.1 mmol) of bromomethylcyclopropane were added thereto. The reaction mixture was stirred at room temperature for 1 hour and then poured into water. The mixture was extracted three times with methylene chloride, the combined organic extracts were washed with water, dried over magnesium sulfate and evaporated. By crystallization of the residue from ethyl acetate and ether there were obtained 4.0 g (84%) of 7-chloro-3-[3-(cyclopropyl-methoxy)- 1-propynyl]-4,5-dihydro-5 methyl6H-imidazo-[1,5-a][1,4]benzodiazepin-6-one of melting point 124-126°.

In an analogous manner, from 7chloro-4,5-dihydro-3-(3-hydroxy-1-propynyl)-5-methyl-6H-imidazo[1,5-a][1,4]-benzodiazepin -6-one (b) with 3-methoxybenzyl chloride there was prepared 7-chloro-4,5-dihydro-3-[3-(3-methoxybenzyloxy)-1-propynyl]-5-methyl-6H-imidazo[1,5-a][1,4]benzodiazepin-6-one of melting point 104-106° (from methylene chloride and hexane);

(c) with 4-methoxybenzyl chloride there was prepared 7-chloro-4,5-dihydro-3-[3-(4-methoxybenzyloxy)-1-propynyl]-5-methyl-6H-imidazo[1,5-a][1,4]benzodiazepin-6-one of melting point 108–110° (from ethyl acetate and hexane);

(d) with benzyl bromide there was prepared 3-[3-(benzyloxy) -1-propynyl]-7-chloro-4,5-dihydro-5-methyl-6H-imidazo[1,5-a][1,4]benzodiazepin-6-one of melting point 108–109° (from methanol and ether):

(e) with bromomethylcyclohexane there was prepared 7-chloro-3-[3-(cyclohexylmethoxy)-1-propynyl]-4,5-dihydro -5-methyl-6H-imidazo[1,5-a][1,4]benzodiazepin-6-one of melting point 68–71° (from ethyl acetate/hexane);

(f) with propargyl bromide there was prepared 7-chloro-4,5-dihydro-5-methyl-3-[3-(3-propynyloxy)-1-propynyl]-6H-imidazo[1,5-a][1,4]benzodiazepin-6-one of melting point 133–134° (from methanol and ether);

(g) with 2-chloroethyl methyl ether there was prepared 7-chloro-4,5-dihydro-3-[3-(2-methoxyethoxy)-1-propynyl]-5-methyl-6H-imidazo[1,5-a][1.4]benzodiazepine-6-one of melting point 105–106° (from methanol and ether).

EXAMPLE 3

(a) 3.73 g (10 mmol) of 7-chloro-4,5-dihydro-3-iodo-5-methyl-6H-imidazo[1,5-a][1,4]benzodiazepin-6-one were mixed with 1.10 g (12 mmol) of 2-methyl-3-butyn-2-ol and 20 ml of diethylamine. Then, 70 mg of bis-(triphenyl -phosphine)-palladium(II) dichloride and 10 mg of copper(I) iodide were added thereto and the mixture was stirred at room temperature for 60 hours. The reaction mixture was evaporated and the residue was dissolved in methylene chloride. The solution was washed twice with water, dried over magnesium sulfate and evaporated. After recrystallization of the residue from ethyl acetate there was obtained 7-chloro-4,5-dihydro-3-(3-hydroxy-3-methyl-1-butynyl)-5-methyl-6H-imidazo[1,5-a][1,4]benzodiazepin-6-one of melting point 193–194°.

By analogy to Example 2, from 7-chloro-4,5-dihydro-3-(3-hydroxy-3-methyl-1-butynyl)-5-methyl-6H-imidazo[1,5-a]-[1,4]benzodiazepin-6-one (b) with 2-chlorobenzyl chloride there was prepared 7-chloro-3-[3-(2-chlorobenzyloxy)-3-methyl-1-butynyl]-4,5-dihydro-5-methyl-6H-imidazo[1,5-a][1,4]benzodiazepin-6-one of melting point 142–143° (from ethyl acetate and hexane);

(c) with 4-chlorobenzyl chloride there was obtained 7-chloro-3-[3-(4-chlorobenzyloxy)-3-methyl-1-butynyl]-4,5-dihydro-5-methyl-6H-imidazo[1,5-a][1,4]benzodiazepin-6-one of melting point 107–108° (from ethyl acetate and hexane):

(d) with 3-chlorobenzyl bromide there was prepared 7-chloro-3-[3-(3-chlorobenzyloxy)-3-methyl-1-butynyl]-4,5-dihydro-5-methyl-6H-imidazo[1,5-a][1,4]benzodiazepin-6-one of melting point 161–163° (from ethyl acetate and hexane);

(e) with benzyl bromide there was prepared 3-[3-(benzyloxy)-3-methyl-1-butynyl]-7-chloro-4,5-dihydro-5-methyl-6H-imidazo[1,5-a][1,4]benzodiazepin-6-one of melting point 143–144° (from ethyl acetate and ether);

(f) with bromomethylcyclopropane there was prepared 7-chloro-3-[3-(cyclopropylmethoxy)-3-methyl-1-butynyl]-4,5-dihydro-5-methyl-6H-imidazo[1,5-a][1,4]benzodiazepin -6-one of melting point 138–140° (from ethyl acetate).

(g) By analogy to Example 1(b). from 7-chloro-4,5-dihydro -3-(3-hydroxy-3-methyl-1-butynyl)-5-methyl-6H-imidazo -[1,5-a][1,4]benzodiazepin-6-one there was prepared 3-(7-chloro-5,6-dihydro-5-methyl-6-oxo-4H-imidazo[1,5-a]-[1,4]benzodiazepin-3-yl)-1,1-dimethyl-2-propynyl cyclopropanecarboxylate of melting point 139–141° (from ethyl acetate and hexane).

EXAMPLE 4

(a) 3.30 g (10 mmol) of 7-chloro-4,5-dihydro-3-(3-hydroxy -3-methyl-1-butynyl)-5-methyl-6H-imidazo[1,5-a][1,4]benzo diazepin-6-one were dissolved in 20 ml of pyridine and treated at room temperature with 1.57 g (13 mmol) of pivaloyl chloride. The reaction mixture was stirred at 65° for 24 hours and then evaporated. The residue was taken up in methylene chloride, the solution was washed once with 1N hydrochloric acid and twice with water, dried over magnesium sulfate and evaporated. By chromatography on silica gel while eluting with ethyl acetate and subsequent crystallization from ethyl acetate and hexane, there was obtained 0.96 g (23%) of 3-(7-chloro-5,6-dihydro-5-methyl -6-oxo-4H-imidazo[1,5-a][1,4]benzodiazepin-3-yl)-1,1-dimethyl-2-propynyl pivalate of melting point 132–133°.

In an analogous manner, from 7-chloro-4,5-dihydro-3-(3-hydroxy-1-butynyl)-5-methyl-6H-imidazo[1,5-a][1,4]-benzodiazepin-6 one:

(b) with acetyl chloride between 4° and room temperature during 2.5 hours there was prepared 3-(7-chloro-5,6-dihydro-5-methyl-6-oxo-4H-imidazo[1,5-a][1,4]benzo -diazepin-3-yl)-1-methyl-2-propynyl acetate of melting point 144–145° (from ethyl acetate and hexane). Yield: 2.86 g (80%);

(c) with cyclopropanecarbonyl chloride between 4° and room temperature, overnight, there was prepared 3-(7-chloro -5,6-dihydro-5-methyl-6-oxo-4H-imidazo[1,5-a][1,4]benzo -diazepin-3-yl)-1-methyl-2-propynyl cyclopropanecarboxylate of melting point 158–160° (from ethyl acetate and hexane). Yield: 2.75 g (71%);

(d) with pivaloyl chloride at 55–60° during 4 hours there was prepared 3-(7-chloro-5,6-dihydro-5-methyl-6-oxo -4H-imidazo[1,5-a][1,4]benzodiazepin-3-yl)-1-methyl-2-propynyl pivalate of melting point 138–140° (from ethyl acetate and hexane). Yield: 2.75 g (84%).

EXAMPLE 5

(a) 7.47 g (20 mmol) of 7-chloro-4,5-dihydro-3-iodo-5-methyl-6H-imidazo[1,5-a][1,4]benzodiazepine-6-one were heated to boiling under reflux for 4 hours with 1.75 g (25 mmol) of 3-butyn-2-ol, 70 mg of bis-(triphenyl -phosphine)-palladium(II) dichloride and 10 mg of copper(I) iodide in 50 ml of diethylamine and 20 ml of ethylene chloride. After evaporation of the solvent the residue was taken up in methylene chloride and the resulting suspension was suction filtered. The material obtained was washed with methylene chloride and, after recrystallization from ethyl acetate, there was obtained 7-chloro -4,5-dihydro-3-(3-hydroxy-1-butynyl)-5-methyl-6H-imidazo -[1,5-a][1,4]benzodiazepin-6-one of melting point 251–252° C.

By analoqy to Example 2 from 7-chloro-4,5-dihydro-3-(3-hydroxy-1-butynyl)-5-methyl-6H-imidazo[1,5-a][1.4]-benzodiazepin-6-one (b) with benzyl bromide there was prepared 3-[3-(benzyloxy)-1-butynyl]-7-chloro-4,5-dihydro-5-methyl-6H -imidazo[1,5-a][1,4]benzodiazepin-6-one of melting point 150–151° (from methylene chloride and hexane). Yield 0.82 g (63%):

(c) with bromomethylcyclopropane at 5° to room temperature during 2.5 hours there was prepared 7- chloro-3-[3-(cyclopropylmethoxy)-1-butinyl]-4,5-dihydro-5-methyl-6H -imidazo[1,5-a][1,4]benzodiazepin-6-one of melting point 138–139° (from methanol and ether). Yield: 2.17 g (58%).

EXAMPLE 6

(a) 25 g (85 mmol) of ethyl 5,6-dihydro-5,7-dimethyl-6-oxo-4H-imidazo[1,5-a][1,4]benzodiazepine-3-carboxylate were heated to boiling under reflux for 1 hour with 3.40 g (85 mmol) of sodium hydroxide in 200 ml of ethanol and 15 ml of water. After evaporation of the ethanol the mixture was diluted with water and acidified with 21 ml of 4 normal hydrochloric acid. The suspension obtained was suction filtered and washed with water. After drying the suction filter cake there was obtained 5,6-dihydro-5,7-dimethyl-6-oxo-4H-imidazo[1,5-a][1,4]benzodiazepine-3-carboxylic acid of decomposition point 274–275°.

(b) 22.20 g (81.8 mmol) of 5,6-dihydro-5,7-dimethyl-6-oxo -4H-imidazo[1,5-a][1,4]benzodiazepine 3-carboxylic acid were heated to 290–300° in a metal bath until the $CO_2$ cleavage had finished. The melt was dissolved in methylene chloride and ethanol and the solution was concentrated until methylene chloride no longer distilled over. 4,5-Dihydro-5,7-dimethyl-6H-imidazo[1,5-a][1,4]benzo -diazepin-6-one of melting point 224–225° crystallized from this solution.

(c) 15.85 g (69.7 mmol) of 4,5-dihydro-5,7-dimethyl-6H -imidazo[1,5-a][1,4]benzodiazepin-6-one were heated to 95° for 2.5 hours with 67 g (264 mmol) of iodine in 100 ml of N,N-dimethylformamide. The reaction mixture was then poured into 450 ml of water, treated with methylene chloride, decolorized with sodium thiosulfate and neutralized with sodium bicarbonate. The aqueous phase was separated and extracted six times with methylene chloride. The combined organic phases were washed three times with water, dried over magnesium sulfate and evaporated. By chromatography of the residue on silica gel while eluting with ethyl acetate and recrystallization from ethyl acetate and hexane, there was obtained 4,5-dihydro-3-iodo-5,7-dimethyl-6H-imidazo[1,5-a][1,4]benzodiazepin-6-one of melting point 106–108°.

(d) 5 g (14.2 mmol) of 4,5-dihydro-3-iodo-5,7-dimethyl-6H -imidazo[1,5-a][1,4]benzodiazepin-6-one were heated to boiling under reflux for 4.5 hours with 1.50 g (17.8 mmol) of 2-methyl-3-butyn-2-ol, 70 mg of bis-(triphenyl -phosphine)-palladium(II) dichloride and 20 mg of copper(I) iodide in 40 ml of diethylamine. The reaction mixture was then evaporated and the residue was chromatographed on silica gel while eluting with ethyl acetate. By recrystallization from ethyl acetate there was obtained 4,5-dihydro-3-(3-hydroxy-3-methyl-1-butynyl)-5,7-dimethyl -6H-imidazo-[1,5-a][1,4]benzodiazepin-6-one of melting point 165–167°.

(e) By analogy to Example 2, from 4,5-dihydro-3-(3-hydroxy-3-methyl-1-butynyl)-5,7-dimethyl-6H-imidazo -[1,5-a][1,4]benzodiazepin-6-one and benzyl chloride there was prepared 3-(3-benzyloxy-3-methyl-1-butynyl)-4,5-dihydro-5,7-dimethyl-6H-imidazo[1,5-a][1,4]benzodiazepin -6-one of melting point 134° (from ethyl acetate and hexane).

EXAMPLE 7

(a) 27.3 g (100 mmol) of (S)-8-chloro-11,12,13,13a-tetra -hydro-9H-imidazo[1,5-a]pyrrolo[2,1-c][1,4]-benzodiazepin -9-one were stirred at 100° for 3 hours with 88 g (350 mmol) of iodine in 200 ml of N,N-dimethylformamide. The reaction mixture was cooled, the separated product was filtered off, rinsed with ethyl acetate and, after drying, there was obtained (S)-8-chloro-11,12,13,13a-tetrahydro-1-iodo-9H-imidazo[1,5-a]pyrrolo[2,1-c][1,4]bendodiazepin-9-one of melting point 298–300°.

(b) 3.99 g (10 mmol) of (S)-8-chloro-11,12,13,13a-tetra hydro-1-iodo-9H-imidazo[1,5-a]pyrrolo[2,1-c][1,4]benzo -diazepin-9-one were stirred at 100° overnight with 0.88 q (10.5 mmol) of 2-methyl-3-butyn-2-ol, 25 mq of palladium(II) acetate, 100 mg of triphenylphosphine and 10 mg of copper(I) iodide in 40 ml of triethylamine and 20 ml of N,N-dimethylformamide. The mixture was then evaporated to dryness and the residue was chromatographed on silica gel while eluting with ethyl acetate. After recrystallization from ethyl acetate there was obtained (S)-8-chloro-11,12,13,13a-tetrahydro-1-(3-hydroxy-3 methyl -1-butynyl)-9H-imidazo[1,5-a]pyrrolo[2,1-c][l,4]benzo -diazepin-9-one of melting point 234–235°.

(c) By analogy to Example 2, from (S)-8-chloro-11,12,13, 13a-tetrahydro-1-(3-hydroxy-3 methyl-1-butynyl)-9H-imidazo [1,5-a]pyrrolo[2,1-c][1,4]benzodiazepin-9-one and benzyl bromide there was prepared (S)-1-(3-benzyloxy-3-methyl-1-butynyl)-8-chloro-11,12,13,13a-tetrahydro-9H-imidazo [1,5-a]pyrrolo[2,1-c][1,4]benzodiazepin-9-one of melting point 146–148° (from ethyl acetate and hexane).

EXAMPLE 8

(a) 7.47 g (20 mmol) of 7-chloro-4,5-dihydro-3-iodo-5-methyl-6H-imidazo[1,5-a][1,4]benzodiazepin-6-one, 2.88 g (30 mmol) of 3-methyl-1-penten-4-yn-3-ol, 110 mg of bis(triphenylphosphine)-palladium(II) dichloride and 35 mg of copper(I) iodide were heated to boiling under reflux for 12 hours in 60 ml of triethylamine and 30 ml of dimethyl-formamide. The reaction mixture was evaporated and the residue was chromatographed on silica gel while eluting with ethyl acetate. By recrystallization of the residue from acetonitrile there was obtained 4.34 g (63%) of 7-chloro-4,5-dihydro-3-(3-hydroxy-3-methyl-4-penten-1-ynyl)-5-methyl-6H-imidazo[1,5-a][1,4-]benzodiazepin-6-one of melting point 185–187°.

In an analogous manner, from 7-chloro-4,5-dihydro 3-iodo-5 methyl-6H-imidazo[1,5-a][1,4]benzodiazepin-6-one (b) with cis-3-methyl-2-penten-4-yn-1-ol there was prepared 7-chloro-4,5-dihydro-3-[(Z)-5-hydroxy-3-methyl-3-penten-1-ynyl]-5-methyl-6H-imidazo[1,5-a][1,4]-benzodiazepin-6-one of melting point 193–194° (from methylene chloride and ethyl acetate);

(c) with trans-3-methyl-2-penten-4-yn-1-ol there was prepared 7-chloro-4,5-dihydro-3-[(E)-5-hydroxy-3-methyl-3-penten-1-ynyl]-5-methyl-6H-imidazo[1,5-a][1,4]-benzodiazepin-6-one of melting point 186–188° (from ethyl acetate and acetonitrile);

(d) with methyl propargyl sulphide and diethylamine in place of triethylamine there was prepared 7-chloro -4,5-dihydro-5-methyl-3-[3-(methylthio)-1-propynyl]-6H -imidazo[1,5-a][1,4]benzodiazepin-6-one of melting point 165–166° (from ethyl acetate);

(e) with 3-butynyl methyl sulphide and diethylamine in place of triethylamine there was prepared 7-chloro -4,5-dihydro-5-methyl-3-[4-(methylthio)-1-butynyl]-6H -imidazo[1,5-a][1,4]benzodiazepin-6-one of melting point 143–145° (from ethyl acetate);

(f) with 2-phenylethyl propargyl ether and diethylamine in place of triethylamine there was prepared 7-chloro -4,5-dihydro-5-methyl-3-[3-(phenethyloxy)-1-propynyl]-6H -imidazo[1,5-a][1,4]benzodiazepin-6-one of melting point 76–78° (from ethyl acetate and hexane).

EXAMPLE 9

(a) 2.31 g (10 mmol) of 8-fluoro-4,5-dihydro-5-methyl-6H -imidazo[1,5-a][1,4]benzodiazepin-6-one were stirred at 95° for 1.5 hours with 8.88 g (35 mmol) of iodine in 25 ml of N,N-dimethylformamide. The reaction mixture was then poured into 300 ml of water, decolorized with sodium thiosulfate solution and extracted four times with methylene chloride. The organic extracts were washed three times with water, dried over magnesium sulfate and evaporated. After recrystallization of the residue from ethyl acetate there was obtained 8-fluoro-4,5-dihydro-3-iodo-5-methyl-6H-imidazo[1,5-a][1,4]benzodiazepin-6-one of melting point 187–188°.

(b) By analogy to Example 8(a), from 8-fluoro-4,5-dihydro -3-iodo-5-methyl-6H-imidazo[1,5-a][1,4]benzodiazepin-6-one, benzyl propargyl ether and diethylamine in place of triethylamine there was prepared 3-[3-(benzyloxy)-1-propynyl]-4.5-dihydro-8-fluoro-5-methyl-6H-imidazo[1,5-a]-[1,4]benzodiazepin-6-one of melting point 90–91° (from ethyl acetate and hexane).

EXAMPLE 10

(a) 19.1 g (56.8 mmol) of 7-bromo-5,6-dihydro-5-methyl-6-oxo-4H-imidazo[1,5-a][1,4]benzodiazepine-3-carboxylic acid were decarboxylated at 290–300°. The melt was taken up in methylene chloride, the solution was diluted with ethyl acetate and ethanol and decolorized with animal charcoal. After evaporation and recrystallization from ethyl acetate and ethanol there was obtained 7-bromo-4,5-dihydro-5-methyl-6H-imidazo[1,5-a][1,4]benzodiazepin-6-one of melting point 196–197°.

(b) 12.80 g (44 mmol) of 7-bromo-4,5-dihydro-5-methyl-6H -imidazo[1,5-a][1,4]benzodiazepin-6-one were stirred at 95° for 3.5 hours with 39 g (154 mmol) of iodine in 80 ml of N,N-dimethylformamide. The reaction mixture was evaporated, the residue was taken up in methylene chloride and water and decolorized by the addition of sodium thiosulfate. The mixture was filtered the organic phase was separated, dried over magnesium sulfate and evaporated. After chromatography of the residue on silica gel while eluting with ethyl acetate, and recrystallization from methylene chloride and ethyl acetate there was obtained 7-bromo-4,5-dihydro-3-iodo-5-methyl-6H-imidazo [1,5-a][1,4]benzodiazepin-6-one of melting point 203–204°.

(c) By analogy to Example 8(a), from 7-bromo-4,5-dihydro -3-iodo-5-methyl-6H-imidazo[1,5-a][1,4]benzodiazepin-6-one, benzyl propargyl ether and diethylamine in place of triethylamine there was prepared 3 [3-(benzyloxy)-1-propynyl]-7-bromo-4,5-dihydro-5-methyl-6H-imidaZo[1,5-a]-[1,4]benzodiazepin-6-one of melting point 106–107° (from methanol and ether).

EXAMPLE 11

By analogy to Example 8(a), from 4,5-dihydro-3-iodo-5-methyl-6H-imidazo[1,5-a][1,4]benzodiazepin-6-one, benzyl propargyl ether and diethylamine in place of triethylamine there was obtained 3-[3-(benzyloxy)-1-propynyl]-4,5-dihydro-5-methyl-6H-imidazo[1,5-a][1,4]benzodiazepin-6-one of melting point 61–63° (from ethanol and ether).

EXAMPLE A

Tablets of the following composition are prepared in the conventional way:

|  | mg/tablet |
|---|---|
| 7-Chloro-3-[3-(cyclopropylmethoxy)-1-propynyl]-4,5-dihydro-5-methyl-6H-imidazo-[1,5-a][1,4]benzodiazepin-6-one | 0.2 |
| Lactose | 140 |
| Maize starch | 50.8 |
| Polyvinylpyrrolidine | 8 |
| Magnesium stearate | 1 |
| Tablet weight | 200 |

EXAMPLE B

Capsules of the following composition are prepared in the conventional way:

|  | mg/capsule |
|---|---|
| 7-Chloro-3-[3-(cyclopropylmethoxy)-1-propynyl]-4,5-dihydro-5-methyl-6H-imidazo-[1,5-a][1,4]benzodiazepin-6-one | 0.5 |
| Lactose | 40 |
| Maize starch | 8 |
| Talc | 1 |
| Magnesium stearate | 0.5 |
| Capsule fill weight | 50 |

EXAMPLE C

Injection solutions of the following composition are prepared in the conventional way:

| 7-Chloro-3-[3-(cyclopropylmethoxy)-1-propynyl]-4,5-dihydro-5-methyl-6H-imidazo-[1,5-a][1,4]benzodiazepin-6-one | 0.1 mg |
|---|---|
| Sodium chloride | 45.0 mg |
| SESQUESTREN Na$_2$ | 0.5 mg |
| Acetic acid p.a. | 0.5 mg |
| NaOH 1N ad pH 4.5 | q.s. |
| Water for injection q.s ad | 5.0 ml |

We claim:

1. A compound of the formula

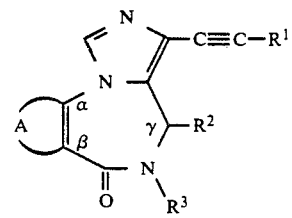

I wherein A together with the two carbon atoms denoted by α and β represents one of the following groups:

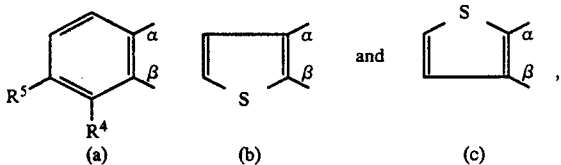

R¹ is a partially unsaturated lower hydrocarbon group having from 2 to 7 carbon atoms which is optionally substituted with hydroxy, oxo, aryl or the group —OR, —SR or —OCOR, or R¹ is a lower alkyl group which is substituted with aryl or the group —OR', —SR' or —OCOR', R and R' each represents aryl or a saturated or partially unsaturated $C_{1-18}$-hydrocarbon group which is optionally substituted with aryl or lower alkoxy, R² is hydrogen, R³ is lower alkyl or R² and R³ together represent dimethylene or trimethylene, R⁴ and R⁵ each represents hydrogen, halogen, trifluoromethyl, cyano, nitro or lower alkyl, the group —OR' being different from lower alkoxy, wherein aryl represents monocyclic aromatic hydrocarbon residues which are unsubstituted or substituted with lower alkyl, lower alkoxy and/or halogen, and the compounds of formula I having the (S)- or (R,S)-configuration with reference to the carbon atom denoted by γ when R² and R³ together represent dimethylene or trimethylene.

2. A compound according to claim 1, wherein R and R' each represents aryl or a saturated or partially unsaturated $C_{1-18}$-hydrocarbon group which is optionally substituted with aryl.

3. A compound according to claim 1, wherein R¹ is a lower alkenyl group which is optionally substituted with hydroxy, oxo, aryl or the group —OR, —SR or —OCOR or a lower alkyl group which is substituted with aryl or the group —OR', —SR' or —OCOR'.

4. A compound according to claim 3, wherein R¹ is a lower alkenyl group which is substituted with hydroxy or the group —OR, —SR or —OCOR or a lower alkyl group which is substituted with the group —OR', —SR' or —OCOR'.

5. A compound according to claim 1, wherein R and R' each represents aryl, aryl-lower alkyl, lower alkoxy-lower alkyl, lower alkyl, $C_{3-7}$-cycloalkyl or $C_{3-7}$-cycloalkyl-lower alkyl.

6. A compound according to claim 1, wherein R² is hydrogen and R³ is methyl, or wherein R² and R³ together represent dimethylene or trimethylene and the carbon atom denoted by γ has the (S)-configuration.

7. A compound according to claim 1, wherein A represents a residue of formula (a) and one of R⁴ and R⁵ is hydrogen and the other is hydrogen or halogen.

8. A compound according to claim 7, wherein R⁴ and R⁵ both are hydrogen or R⁴ is hydrogen and R⁵ is fluorine, or R⁴ is chlorine or bromine and R⁵ is hydrogen.

9. A compound according to claim 1, which is 7-Chloro-3-[3-(cyclopropylmethoxy)-1-propynyl]-4,5-dihydro-5-methyl-6H-imidazo[1,5-a][1,4]benzodiazepin-6-one.

10. A compound according to claim 1, which is 3-(7-Chloro-5,6-dihydro-5-methyl-6-oxo-4H-imidazo -[1,5-a][1,4]benzodiazepin-3-yl)-2-propynyl acetate.

11. A compound according to claim 1, which is 7-Chloro-3-[3-(cyclopropylmethoxy)-3-methyl-1-butynyl]-4,5-dihydro-5-methyl-6H-imidazo[1,5-a][1,4]benzo -diazepin-6-one.

12. A compound according to claim 1, which is 7-Chloro-4,5-dihydro-3-[(Z)-5-hydroxy-3-methyl-3-penten-1-ynyl]-5-methyl-6H-imidazo[1,5-a][1,4]benzo-diazepin-6-one.

13. A compound according to claim 1, which is 7-Chloro-4,5-dihydro-3-(3-hydroxy-3-methyl-4-penten-1-ynyl)-5-methyl-6H-imidazo[1,5-a][1,4]benzo -diazepin-6-one.

14. A compound according to claim 1, which is 7-Chloro-4,5-dihydro-3-[(E)-5-hydroxy-3-methyl-3-penten-1-ynyl]-5-methyl-6H-imidazo[1,5-a][1,4]benzo -diazepin-6-one.

15. A pharmaceutical composition which comprises a therapeutically effective amount of a compound of the formula

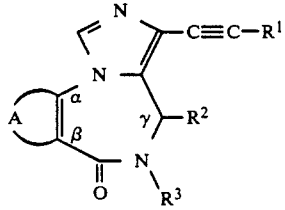

wherein A together with the two carbon atoms denoted by α and β represents one of the following groups:

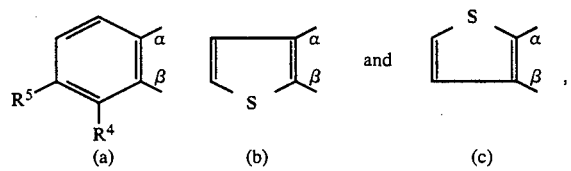

R¹ is a partially unsaturated lower hydrocarbon group having from 2 to 7 carbon atoms which is optionally substituted with hydroxy, oxo, aryl or the group —OR, —SR or —OCOR, or R¹ is a lower alkyl group which is substituted with aryl or the group —OR', —SR' or —OCOR', R and R' each represents aryl or a saturated or partially unsaturated $C_{1-18}$-hydrocarbon group which is optionally substituted with aryl or lower alkoxy, R² is hydrogen, R³ is lower alkyl or R² and R³ together represent dimethylene or trimethylene, R⁴ and R⁵ each represents hydrogen, halogen, trifluoromethyl, cyano, nitro or lower alkyl, the group —OR' being different from lower alkoxy, wherein aryl represents monocyclic aromatic hydrocarbon residues which are unsubstituted or substituted with lower alkyl, lower alkoxy and/or halogen, and the compounds of formula I having the (S)- or (R,S)-configuration with reference to the carbon atom denoted by γ when R² and R³ together represent dimethylene or trimethylene, and a pharmaceutically inert carrier.

16. A composition according to claim 15, wherein R and R' each represents aryl or a saturated or partially unsaturated $C_{1-18}$-hydrocarbon group which is optionally substituted with aryl.

17. A composition according to claim 15, wherein R¹ is a lower alkenyl group which is optionally substituted with hydroxy, oxo, aryl or the group —OR, —SR or —OCOR or a lower alkyl group which is substituted with aryl or the group —OR', —SR' or —OCOR'.

18. A composition according to claim 17, wherein R¹ is a lower alkenyl group which is substituted with hydroxy or the group —OR, —SR or —OCOR or a lower alkyl group which is substituted with the group —OR', —SR' or —OCOR'.

19. A composition according to claim 15, wherein R and R' each represents aryl, aryl-lower alkyl, lower alkoxy-lower alkyl, lower alkyl, $C_{3-7}$-cycloalkyl or $C_{3-7}$-cycloalkyl-lower alkyl.

20. A composition according to claim 15, wherein $R^2$ is hydrogen and $R^3$ is methyl, or wherein $R^2$ and $R^3$ together represent dimethylene or trimethylene and the carbon atom denoted by $\gamma$ has the (S)-configuration.

21. A composition according to claim 15, wherein A represents a residue of formula (a) and one of $R^4$ and $R^5$ is hydrogen and the other is hydrogen or halogen.

22. A composition according to claim 21, wherein $R^4$ and $R^5$ both are hydrogen or $R^4$ is hydrogen and $R^5$ is fluorine, or $R^4$ is chlorine or bromine and $R^5$ is hydrogen.

23. A composition according to claim 15, in which the compound is 7-Chloro-3-[3-(cyclopropylmethoxy)-1-propynyl]-4,5-dihydro-5-methyl-6H-imidazo[1,5-a][1,4]benzodiazepin-6-one.

24. A composition according to claim 15, in which the compound is 3-(7-Chloro-5,6-dihydro-5-methyl-6-oxo-4H-imidazo-[1,5-a][1,4]benzodiazepin-3-yl)-2-propynyl acetate.

25. A composition according to claim 15, in which the compound is 7-Chloro-3-[3-(cyclopropylmethoxy)-3-methyl-1-butynyl]-4,5-dihydro-5-methyl-6H-imidazo[1,5-a][1,4]benzo-diazepin-6-one.

26. A composition according to claim 15, in which the compound is 7-Chloro-4,5-dihydro-3-[(Z)-5-hydroxy-3-methyl-3-penten-1-ynyl]-5-methyl-6H-imidazo[1,5-a][1,4]benzo-diazepin-6-one.

27. A composition according to claim 15, in which the compound is 7-Chloro-4,5-dihydro-3-(3-hydroxy-3-methyl-4-penten-1-ynyl)-5-methyl-6H-imidazo[1,5-a][1,4]benzo-diazepin-6-one.

28. A composition according to claim 15, in which the compound is 7-Chloro-4,5-dihydro-3-[(E)-5-hydroxy-3-methyl-3-penten-1-ynyl]-5-methyl-6H-imidazo[1,5-a][1,4]benzo-diazepin-6-one.

29. A composition according to claim 15 wherein compound I is present in an amount which is effective in treating convulsions.

30. A composition according to claim 15 wherein compound I is present in an amount which is effective in treating anxiety states.

31. A composition according to claim 15 wherein compound I is present in an amount which is effective in treating stress condition.

32. A composition according to claim 15 wherein compound I is present in an amount which is effective in treating excitation states.

33. A composition according to claim 15 wherein compound I is present in an amount which is effective in treating sleep disorders.

* * * * *

UNITED STATES PATENT AND TRADEMARK OFFICE
CERTIFICATE OF CORRECTION

PATENT NO. : 5,021,411

DATED : June 4, 1991

INVENTOR(S) : Hunkeler et al.

It is certified that error appears in the above-identified patent and that said Letters Patent is hereby corrected as shown below:

On the title page, under "[56]   References Cited

U.S. PATENT DOCUMENTS"

delete "4,803,920" and insert therefor -- 4,863,920 --.

Signed and Sealed this

Fifteenth Day of December, 1992

Attest:

DOUGLAS B. COMER

*Attesting Officer*  *Acting Commissioner of Patents and Trademarks*